US010028782B2

(12) United States Patent
Orion (10) Patent No.: US 10,028,782 B2
(45) Date of Patent: Jul. 24, 2018

(54) METHOD AND APPARATUS FOR THROMBUS DISSOLUTION/THROMBECTOMY BY AN ELECTRODE CATHETER DEVICE (75) Inventor: Itzhak Orion, Lehavim (IL)

(73) Assignee: MAGNETO THROMBECTOMY SOLUTIONS LTD., Ariel (IL)

( * ) Notice: Subject to any disclaimer, the term of this patent is extended or adjusted under 35 U.S.C. 154(b) by 932 days.

(21) Appl. No.: 13/127,118

(22) PCT Filed: Nov. 3, 2009

(86) PCT No.: PCT/IL2009/001024
§ 371 (c)(1),
(2), (4) Date: Aug. 23, 2011

(87) PCT Pub. No.: WO2010/061376
PCT Pub. Date: Jun. 3, 2010

(65) Prior Publication Data
US 2011/0301594 A1 Dec. 8, 2011

Related U.S. Application Data (60) Provisional application No. 61/193,166, filed on Nov. 3, 2008.

(51) Int. Cl.
A61B 18/00 (2006.01)
A61B 18/14 (2006.01)
(Continued)

(52) U.S. Cl.
CPC .......... *A61B 18/1492* (2013.01); *A61B 90/39* (2016.02); *A61B 2018/0041* (2013.01);
(Continued)

(58) Field of Classification Search
CPC . A61B 18/18; A61B 18/1815; A61B 2018/18; A61B 2018/1815;
(Continued)

(56) References Cited

U.S. PATENT DOCUMENTS 4,027,674 A 6/1977 Tessler et al.
5,122,136 A 6/1992 Guglielmi
(Continued)

FOREIGN PATENT DOCUMENTS

EP 1329196 A1 7/2003
WO 0124720 A1 4/2001

OTHER PUBLICATIONS

Gralla, J. et al., "A Dedicated Animal Model for Mechanical Thrombectomy in Acute Stroke", American Journal of Neuroradiology, vol. 27, pp. 1357-1361, 2006.
(Continued)

*Primary Examiner* — Jaymi Della
*Assistant Examiner* — Eunhwa Kim
(74) *Attorney, Agent, or Firm* — D. Kligler IP Services Ltd.

(57) ABSTRACT

The present invention generally relates to a flexible catheter device capable of being introduced into body passages, withdraw fluids therefrom or introduce fluids thereinto, and which includes electrodes configured to apply electrical signals in the body passage for carrying out thrombus dissolution and/or thrombectomy, wherein one of said electrodes is designed to contact the thrombus material and remove it or dissolve it, and wherein the electrical voltage signals are a unipolar pulsatile voltage signal.

13 Claims, 8 Drawing Sheets (51) Int. Cl.
*A61B 18/02* (2006.01)
*A61B 18/12* (2006.01)
*A61B 90/00* (2016.01)

(52) U.S. Cl.
CPC .............. *A61B 2018/00166* (2013.01); *A61B 2018/00404* (2013.01); *A61B 2018/00416* (2013.01); *A61B 2018/00422* (2013.01); *A61B 2018/00428* (2013.01); *A61B 2018/0212* (2013.01); *A61B 2018/1266* (2013.01); *A61B 2018/1435* (2013.01)

(58) Field of Classification Search
CPC .... A61B 2018/1846; A61B 2018/1838; A61B 2018/1853; A61B 2018/1861; A61B 2018/1892; A61B 2018/0041; A61B 2018/00416; A61B 2018/00422; A61B 2018/00428; A61B 17/1215; A61B 17/12177; A61B 2017/22084; A61B 2018/162
USPC ........................................................... 606/41
See application file for complete search history.

(56) References Cited

U.S. PATENT DOCUMENTS

| | | | |
|---|---|---|---|
| 5,125,928 A | | 6/1992 | Parins et al. |
| 5,300,068 A | * | 4/1994 | Rosar et al. ................. 606/34 |
| 5,507,743 A | * | 4/1996 | Edwards et al. ............. 606/41 |
| 5,569,204 A | * | 10/1996 | Cramer ..................... 604/164.1 |
| 5,603,731 A | | 2/1997 | Whitney |
| 5,851,206 A | * | 12/1998 | Guglielmi ........ A61B 17/12022 606/28 |
| 5,925,042 A | * | 7/1999 | Gough et al. ................. 606/41 |
| 6,047,700 A | | 4/2000 | Eggers et al. |
| 6,210,404 B1 | | 4/2001 | Shadduck |
| 6,554,827 B2 | * | 4/2003 | Chandrasekaran et al. .... 606/41 |
| 6,658,288 B1 | | 12/2003 | Hayashi |
| 8,197,478 B2 | | 6/2012 | Hayashi et al. |
| 8,814,859 B2 | | 8/2014 | Drasler et al. |
| 2001/0001314 A1 | | 5/2001 | Davison et al. |
| 2002/0058937 A1 | * | 5/2002 | Maltese ......................... 606/41 |
| 2002/0072764 A1 | * | 6/2002 | Sepetka et al. ............... 606/200 |
| 2002/0133111 A1 | | 9/2002 | Shadduck |
| 2003/0050634 A1 | * | 3/2003 | Ellman et al. ................. 606/41 |
| 2003/0125787 A1 | * | 7/2003 | Shchervinsky ............... 607/132 |
| 2003/0130571 A1 | * | 7/2003 | Lattouf ............ A61B 17/00234 600/374 |
| 2004/0073243 A1 | | 4/2004 | Sepetka et al. |
| 2005/0159739 A1 | * | 7/2005 | Paul et al. ..................... 606/41 |
| 2007/0156082 A1 | * | 7/2007 | Scherman ............. A61N 1/327 604/20 |
| 2007/0255270 A1 | | 11/2007 | Carney |
| 2008/0161796 A1 | * | 7/2008 | Cao et al. ..................... 606/41 |
| 2008/0161803 A1 | | 7/2008 | Oral et al. |
| 2008/0161893 A1 | | 7/2008 | Paul et al. |
| 2008/0262489 A1 | * | 10/2008 | Steinke ......................... 606/33 |
| 2012/0296262 A1 | | 11/2012 | Ogata et al. |

OTHER PUBLICATIONS

Sawyer, P.N. et al., "Electrical Hemostasis in Uncontrollable Bleeding States", Annals of Surgery, vol. 154, No. 4, Oct. 1961.
P. N. Sawyer et al., "Electrical hemostasis in uncontrollable bleeding states", Annals of Surgery 154 (4) Oct. 1961.
J. Gralla et al., "A dedicated animal model for mechanical thrombectomy in acute stroke", AJNR Am. J. Neuroradiol. 27:1357-61, Jun.-Jul. 2006.
European Application # 17151831.3 Search Report dated May 22, 2017.
International Application # PCT/IB2018/050010 Search Report dated May 10, 2018.

* cited by examiner

METHOD AND APPARATUS FOR THROMBUS DISSOLUTION/THROMBECTOMY BY AN ELECTRODE CATHETER DEVICE

FIELD OF THE INVENTION

The present invention relates to removal and/or dissolution of thrombus from blood vessels by application of electrical fields. More particularly, the invention relates to a method and apparatus for thrombus dissolution and/or thrombectomy utilizing electrodes provided in a catheter device by endovascular angiographic catheterization procedure.

BACKGROUND OF THE INVENTION

Blood clot (thrombus), generated in blood vessels (arteries or veins), by activation of blood coagulation cascade and culminates in the generation of thrombin at the site together with platelet aggregation, resulting in formation of a blood clot composed of platelets and fibrin. The coagulation process of the blood clot involves charged proteins, enzymes, phospholipids and mineral ions, and platelets. Therefore, electrostatic forces may act on the clot by these components, protein enzymes activity and structural conformation changes. It was shown in previous experiments by Sawyer [P. N. Sawyer, et al., "Electrical Hemostasis in Uncontrollable Bleeding States", Annals of Surgery 154 (4) October 1961] that the positive electrode of a direct current electrode pair applied to the surface of a blood vessel can produce thrombosis that is attached to the positive electrode.

Various examples for using electrodes in blood vessels and other body passages or organs are known from the patent literature.

U.S. Pat. No. 4,027,674 describes a method and device for removing concretions within human ducts. The catheterization device used in this patent comprises an axially positioned flexible positive electrode together with a flexible negative electrode which are adapted for applying high voltage pulses with low currents for removing concretions from the urinary tract or the kidney. While this arrangement can be used for urinary tract treatments the pulse shape and amplitude suggested are too energetic for clot dissolution in blood vessels, and thus not suitable for such applications.

US Pat. No. 6,210,404 describes a design for producing energy power (heat) micro-catheter system to be delivered into a thrombus by generating acoustic waves due to high repetition rate of expansion and collapse of media. This design is based only on electro-thermal or electro-mechanical effects, and it aims to disassociate the thrombus by the acoustic waves traveling from the catheter site into the thrombus. This system relies on generation of bubbles that will project or "jet" the Pharmacologic agent at a controlled velocity into the acoustically disrupted thrombus to further de-polymerize the thrombus.

The apparatus described in U.S. Pat. No. 6,658,288 is designed for aiding thrombosis processes at a treatment site of a patient through the application of electric potential for repairing a blood vessel. The apparatus includes an elongated hollow prosthesis for placement within a blood vessel, said hollow prosthesis comprises an inner and outer surfaces, wherein an electric potential difference may be created between said surfaces.

An endovascular electrolytically detachable guidewire tip for the electroformation of thrombus in arteries is described in U.S. Pat. No. 5,122,136 and EP1329196. In these patent publications the guidewire used comprises a core wire having a distal portion susceptible to electrolytic disintegration in blood, where the distal portion is an exposed stainless steel segment comprising a coil connected at its proximate end to the core wire. In use, the distal tip of the guidewire is disposed in a vascular cavity and an electrical signal is applied to the distal tip to form a thrombus about the distal tip. The distal tip is then detached from the guidewire and left within the vascular cavity with the thrombus electrically formed thereabout.

U.S. Pat. No. 5,603,731 describes a method for preventing thrombosis by means of an expandable stent placed in a blood vessel and which act as a conductor on which electronegative potential is imposed by means of an electronegative generator implemented by a microwave detector diode incorporated in the stent structure. The microwave detector diode incorporated in the stent structure is designed to be operated from outside of the patient's body by the application of microwaves.

The methods described above have not yet provided satisfactory solutions for removal or dissolution of thrombus formation in blood vessels. Therefore there is a need for improved catheter designs and methods capable of removing thrombus from blood vessels or other body passages or organs.

It is therefore an object of the present invention to provide a method and apparatus for removal and/or dissolution of thrombus blood vessel by means of electrical fields.

It is another object of the present invention to provide a catheter device comprising electrodes designed for introduction into blood vessels or other body passages or organs for contacting and removing/retrieving a thrombus.

It is a further object of the present invention to provide procedures for introducing electrodes comprised in a catheter device into blood vessels or other body passages of a patient and applying electrical fields therein for removing thrombus material therefrom.

It is yet another object of the present invention to provide a method and catheter device for collecting blood clots and removing them from a blood vessel.

An additional object of the present invention is to provide a catheter device and methods for using it to open blocked body passages in a treated subject.

Other objects and advantages of the invention will become apparent as the description proceeds.

SUMMARY OF THE INVENTION

The inventor of the present invention has designed a new electrode catheter device and methods for carrying out thrombus dissolution and/or thrombectomy/retrieval by applying electrical fields via electrodes provided in said device, where one of said electrodes is designed to contact the thrombus material and remove it or dissolve it. The inventor hereof found that the application of electrical pulses can be effectively used to dissolve a clot (i.e., a thrombolysis process) in a blood vessel system by contacting a negatively charged electrode with a thrombus. Furthermore, the inventor has found that thrombotic material can be partially or completely removed from a thrombotic mass present in a blood vessel by contacting a positively charged electrode with the thrombus and retracting said electrode together with the attached thrombotic material proximally via the catheter device. It has further been found that the process of thrombus dissolution and/or breakdown and removal may be significantly accelerated when the thrombus-contacting electrode is fed with a pulsatile voltage signal.

The term electrode catheter used herein generally relates to a flexible catheter device capable of being introduced into body passages, withdraw fluids therefrom or introduce fluids thereinto, and which includes electrodes configured to apply electrical voltage signals in the body passage.

According to one preferred embodiment the electrode catheter of the invention is made from a flexible elongate tube having proximal and distal ends and comprising at least two lumens through which first and a second electrically conducting wires are respectively passed, wherein the first wire is electrically coupled to a thrombus-contacting electrode having a straight, spiral, helical or curly, end section (e.g., comprising about 20-30 loops) situated at the distal end of the catheter device, and wherein the second wire is electrically coupled to an internal electrode placed in a distal section of the lumen in which said second wire is passed. The thrombus-contacting electrode and the internal electrode are preferably arranged such that a gap of about 2 to 30 mm is obtained between their distal tips (i.e., the distance along the longitudinal axis of the catheter device). The electrode catheter may further comprise a proximal lateral access port configured in fluid communication with one or more lumens of said catheter for allowing removal of blood, debris and clots, therethrough.

The distal section of the lumen in which the internal electrode is located is advantageously configured to have a relatively large cross sectional area in order to allow improved contact between the internal electrode and the blood in the treated site. Furthermore, the internal electrode may be configured such that its contact with the blood in the treated vessel is maximized inside the catheter lumen. Thus, in one preferred embodiment, the internal electrode may be configured in the form of a brush comprising a plurality of electrical conducting bristles. One or both of the electrically conducting wires are preferably covered with an electrically isolating material applied along substantial portions of their lengths in order to prevent discharging of electrical charges from the wires.

According to another preferred embodiment the electrode catheter of the invention is made from a flexible elongate tube having proximal and distal ends and comprising a single lumen in which both a first and a second electrically conducting wires are passed, wherein the first wire is electrically coupled to a thrombus-contacting electrode having a straight, spiral, helical or curly end section situated at the distal end of the catheter device, and wherein the second wire is electrically coupled to an internal electrode placed in a distal section of the lumen. The thrombus-contacting electrode and the internal electrode are preferably arranged such that a gap of about 2 to 30 mm (i.e., the longitudinal distance between tips) is obtained between their distal tips. The electrically conducting wires may be placed one adjacent the other inside the lumen where the wires are preferably electrically isolated in order to prevent passage of electrical currents between them. The electrode catheter may further comprise a lateral access port configured in fluid communication with the lumen of the electrode catheter for allowing removal of blood, debris and clots, therethrough.

The second wire electrically coupled to the internal electrode may be wound in a helical or other fashion over the first wire, or alternatively, it may comprise a plurality of electrically conducting strands braided over the first wire.

These arrangements may be advantageously used to dissolve or remove thrombus material from a blood vessel by applying, via the electrodes, unipolar voltage signals having relatively low voltages (1 to 100 volts) and having low or high frequencies (0.1 Hz to 100 Mhz).

In operation, the electrode catheter of the invention is introduced into the vascular system of the treated subject via a standard endovascular angiographic catheterization procedure and advanced into the treatment site by utilizing a guiding sheath/catheter and/or guide-wire. The thrombus-contacting electrode is arranged such that its distal section contacts the thrombus material while maintaining a gap (longitudinal distance) of about 2 to 30 mm between its distal tip and the distal tip of the internal electrode. In this state, in a dissolution procedure, voltage signals are applied via the electrodes such that the internal electrode delivers positive electrical charges into the treatment site and the thrombus contacting electrode delivers negative electrical charges into the treatment site, thereby causing dissolution of the thrombus and trapping of the dissolved or partially-dissolved thrombus material within the internal electrode. Dissolved thrombus material may be removed via the lateral access, port, or alternatively, whenever the internal electrode becomes covered by the dissolved thrombus material it may be retracted proximally and remove from the body of the treated subject and then cleaned or replaced for dissolving more thrombus material, if so needed.

In the case of a thrombectomy procedure, after placing the electrode catheter in the treatment site and contacting the thrombus material with the distal section of the thrombus-contacting electrode, voltage signals are applied via the electrodes such that the thrombus-contacting electrode delivers positive electrical charges into the treatment site thereby causing said electrode to become attached to the thrombus material, and the internal electrode delivers negative electrical charges into the treatment site. After a sufficient period of time for establishing satisfactory attachment with the thrombus material has passed (e.g., 1 to minutes, preferably about 5 minutes) the thrombus-contacting electrode is retracted proximally into the electrode catheter, thereby opening the blockage caused by the thrombus material and removing portion thereof, or the entire thrombus. Alternatively, once sufficient attachment is obtained between the thrombus-contacting electrode and the thrombus material the electrode catheter is retracted proximally with its electrodes such that the blockage caused by the thrombus material is opened and a portion thereof, or the entire thrombus, is removed.

The electrical signal applied via the electrodes of the electrode catheter is preferably a periodic signal comprising unipolar wave forms. For example, the electrical signal may comprise the positive half waves of a sinusoidal signal. Advantageously, a unipolar periodic pulse signal is used. Preferably, the waveform of the pulses in the unipolar periodic pulse signal has a trapezoidal shape.

According to one aspect the present invention in directed to a catheter device comprising at least one lumen passing along its length in which first and second electrically conducting wires are passed, wherein the distal end of the first wire is electrically coupled to a thrombus-contacting electrode having a curly, helical or spiral, end section (e.g., comprising 20-30 helix/spiral loops), and wherein the second wire is electrically coupled to an internal electrode placed in a distal section of the lumen. The catheter device may further comprise a lateral access port configured in fluid communication with its lumen.

Preferably, the thrombus-contacting electrode and the internal electrode are arranged such that a longitudinal gap of about 2 to 30 mm is obtained between their distal tips. Advantageously, one or both of the electrically conducting wires are covered by an electrically isolating material.

According to one specific preferred embodiment the second wire is wound in a helical or other fashion over the first wire. Additionally or alternatively, the second wire may comprise a plurality of electrically conducting strands braided over the first wire.

According to another preferred embodiment of the invention the catheter device comprises at least two lumens passing along its length, wherein each of the electrically conducting wires is passed in one of the at least two lumens such that the internal electrode is placed inside the distal sections of one of the lumens. The catheter device may further comprise a proximal lateral access port configured in fluid communication with at least one of its lumens. Advantageously, the cross sectional area of the distal section in which the internal electrode is placed is greater than the cross sectional area of the lumen leading to it.

According to one specific preferred embodiment of the invention the internal electrode is configured in a form of a brush comprising a plurality of electrical conducting bristles.

The various embodiments of the catheter device of the invention may be used for dissolving or removing thrombus material from a blood vessel by applying unipolar voltage signals via the electrodes, said voltage signals are being relatively low (1 to 100 volts) in order to eliminate possible damages of body passages or organs. Preferably, the unipolar voltage signal is a periodic signal having a frequency in the range of 0.1 Hz to 100 Mhz.

According to another aspect the present invention is directed to a method for dissolving thrombus material in a blood vessel or organ of a living subject by means of the catheter device described hereinabove or hereinbelow, the method comprising:
Introducing into the vascular system of the treated subject the catheter device via a standard endovascular angiographic catheterization procedure;
Advancing the catheter device until its distal end reaches the treatment site comprising the thrombus material;
Arranging the thrombus-contacting electrode such that its distal section contacts the thrombus material while maintaining a longitudinal distance of about 2 to 30 mm between the distal tips of the electrodes; and
Applying voltage signals via the electrodes such that the internal electrode delivers positive electrical charges into the treatment site.

The method may further comprise removing dissolved thrombus material via the lateral access port during the procedure. Additionally or alternatively, the method may further comprise retracting proximally and removing the internal electrode from the body of the treated subject whenever it becomes covered by the dissolved thrombus material, and cleaning or replacing it for dissolving more thrombus material, if so needed.

According to yet another aspect the present invention is directed to a method for removing thrombus material from a blood vessel or from an organ of a living subject by means of the catheter device described hereinabove or hereinbelow, the method comprising:
Introducing into the vascular system of the treated subject the catheter device via a standard endovascular angiographic catheterization procedure;
Advancing the catheter device until its distal end reaches the treatment site comprising the thrombus material;
Arranging the thrombus-contacting electrode such that its distal section contacts the thrombus material and a longitudinal distance of about 2 to 30 mm is obtained between its distal tip and the distal tip of the internal electrode;
Applying voltage signals via the electrodes such that the thrombus-contacting electrode delivers positive electrical charges into the treatment site thereby causing it to become attached to the thrombus material; and
Retracting the thrombus-contacting electrode proximally into the catheter device and removing it from the body of the treated subject.

Advantageously, the electrical signals applied via the electrodes of the catheter device are periodic unipolar signals (e.g., comprising positive half waves of a sinusoidal signal). Preferably, the periodic unipolar signals are unipolar pulse signals having a trapezoidal waveform shapes.

BRIEF DESCRIPTION OF THE DRAWINGS

The present invention is illustrated by way of example in the accompanying drawings, in which similar references consistently indicate similar elements and in which:

FIGS. 1A to 1D illustrate preferred embodiments of a catheter apparatus of the invention comprising electrodes and an exemplary voltage signal suitable for dissolution/thrombectomy procedures, wherein FIG. 1A shows a sectional view of the catheter device, FIG. 1B demonstrates a thrombectomy procedures, FIG. 1C demonstrates a dissolution procedure, and FIG. 1D illustrates a voltage signal suitable for dissolution/thrombectomy procedures using the catheter device of the invention;

It is noted that the embodiments exemplified in the figures are not intended to be in scale and are in diagram form to facilitate ease of understanding and description.

DETAILED DESCRIPTION OF PREFERRED EMBODIMENTS

The present invention provides a method and apparatus for removal and/or dissolution of thrombus from a blood vessel by means of electrically charged electrodes provided in a catheter device. Procedures for removal and/or dissolution of thrombus material are described wherein an electric field is induced within the lumen of the infarcted blood vessel of the patient, for a sufficient time, to cause lysis of the clot.

Figure 1A:
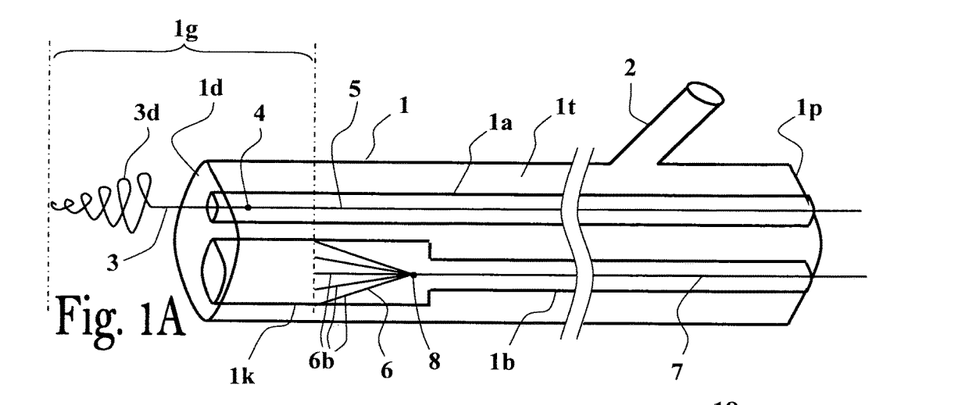

FIG. 1A schematically illustrates one preferred embodiment of a catheter device 1 of the invention. Catheter device 1 is preferably made from a flexible and electrically inert tube 1t having a proximal end 1p and a distal end 1d, and which may comprise at least two lumens 1a and 1b passing along the entire length of the catheter device 1.

A thrombus-contacting electrode 3 (also referred to herein as treatment electrode) is attached at distal end 1d of catheter device 1 such that distal portion 3d thereof protrudes distally from a distal end opening of lumen 1a. Thrombus-contacting electrode 3 is electrically coupled at connection point 4 to an electrically conducting wire 5 passing in lumen 1*a*. The distal portion 3*d* of thrombus-contacting electrode 3 may be provided in a form of a straight wire, preferably, it is formed in a helical, spiral or curly, shape in order to increase the contact area obtained therewith when pressed against thrombus material in a blood vessel or other body passage.

Catheter device 1 further comprises an internal electrode 6 electrically coupled to an electric conducting wire 7 passing along lumen 1*b*. Internal electrode 6 may be placed inside a lumen having the same configuration as of lumen 1*b*, preferably, it is disposed inside a distal section 1*k* of lumen 1*b* which may have a relatively greater inner diameter adapted for accommodating internal electrode 6. Internal electrode 6 is preferably configured to provide an enlarged surface area for contacting the blood in the vessel or body passage wherein the treated thrombus is located. According to one preferred embodiment internal electrode 6 is made in a form of a brush comprising a plurality of electric conducting bristles 6*b* electrically coupled to wire 7 at connection point 8. The internal electrode 6 and wire 7 assembly is preferably configured to be retractable to allow its removal and/or replacement during a thrombus treatment procedure, if so needed.

Catheter device 1 may further comprise a proximal lateral accession port 2 for drawing backward blood with debris and bubbles, which may be generated during the treatment process, by means of a syringe (not shown) or by using other devices suitable for this purpose. Lateral accession port 2 may be configured to be in fluid communication with lumen 1*a* or 1*b*, or with both lumens of catheter device 1.

In a typical treatment procedure catheter device 1 with its wires, 5 and 7, and electrodes, 3 and 6, is introduced into the vascular system via a standard endovascular angiographic catheterization procedure. The catheter tip is preferably introduced into a blood vessel being as close as possible to the thrombus to be treated.

By way of example, the body of catheter device 1 may be specifically designed to meet requirements of a treatment procedure, or alternatively implemented by a number of different commercially-available devices including: Prowler 10, 14, and Plus (Cordis Corp.), Echelon 10 and 14 (Micro Therapeutics, Inc., Irvine, Calif., U.S.), or the Excelsior SL-10 and 1018 (Target Therapeutics/Boston Scientific, Fremont, Calif., U.S.) micro-catheters as used for aneurysm coil embolization and IA infusions. Additionally or alternatively, clot retrieval devices may be combined in catheter device 1, such as, but not limited to, the Merci Retrieval System (Concentric Medical, Inc., Mountain View, Calif., U.S.).

The catheter device 1 may become occluded with thrombus during the treatment process e.g., thrombus material generated in situ on the positive electrode, and in such cases lateral side access port 2 may be used for connecting a syringe, or other such device, for drawing backward some blood containing debris and/or bubbles generated during the process. The ability to draw blood back is important for maintaining the desired closed electrical circuit conditions which is a basic requirement in the thrombectomy/dissolution procedures of the invention.

In cases wherein the thrombus material is not fully dissolved, catheter 1 may be retracted proximally from the blood vessel for cleaning, or alternatively, it may be replaced by a new operative catheter 1 that will be introduced into the same treatment site for further operation.

Figure 1B:
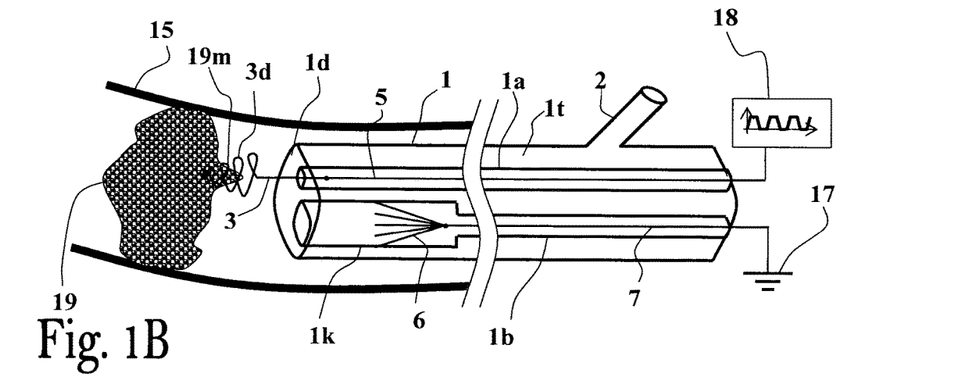

FIG. 1B demonstrates a thrombectomy procedures carried out using catheter device 1 illustrated in FIG. 1A. In this example internal electrode 6 is electrically grounded by connecting the proximal tip of wire 7 to suitable grounding means 17 (e.g., the grounding provided by the local electricity system, or alternatively the patient's bed or body), and the distal portion 3*d* of thrombus-contacting electrode 3 is used for applying a positive voltage signal (e.g., 10 in FIG. 1D) by connecting the proximal tip of wire 5 to a suitable positive electrical power source 18. As demonstrated in FIG. 1B, during this process distal portion 3*d* of thrombus-contacting electrode 3 is pressed against the thrombus 19 blocking the treated blood vessel 15, and due to its positive potential it becomes covered by thrombus material 19*m*. During this process distal portion 3*d* of thrombus-contacting electrode 3 further becomes attached to thrombus 19 thus allowing retrieving portions of the thrombus material, or the entire thrombus 19, by retracting thrombus-contacting electrode 3 proximally via lumen 1*a*, and thereby opening a passage through the blocked blood vessel 15. Alternativley, both of the electrodes, rather than just electrode 3, may be withdrawn proximally. In an alternative preferred embodiment of the invention, the entire catheter (including the electrode assembly), rather than just electrode 3, may be withdrawn proximally.

Figure 1C:
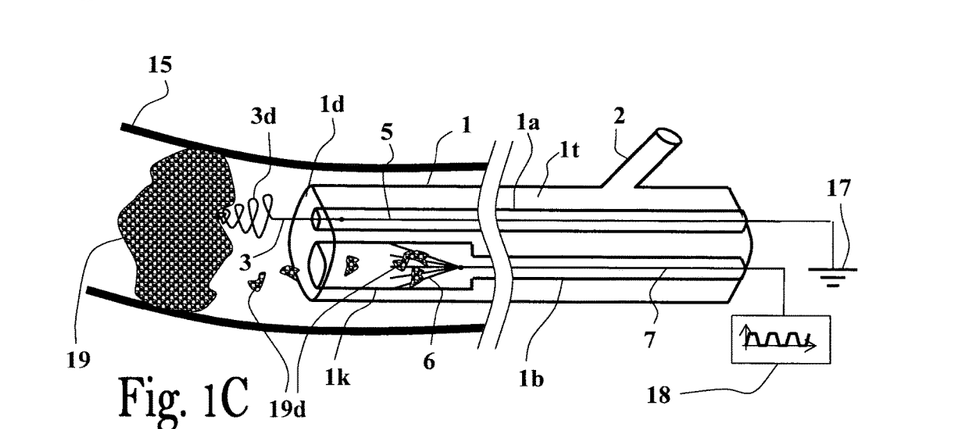

FIG. 1C demonstrates a dissolution procedure carried out using catheter device 1 illustrated in FIG. 1A. In this example thrombus-contacting electrode 3 is electrically grounded by connecting the proximal tip of wire 5 to suitable grounding means 17 (e.g., grounding of the local electricity system, or the patient's bed or body), and internal electrode 6 is used for applying a positive voltage signal (e.g., 10 in FIG. 10) by connecting the proximal tip of wire 7 to a suitable positive electrical power source 18. As demonstrated in FIG. 1C, during this process distal portion 3*d* of thrombus-contacting electrode 3 is pressed against the thrombus 19 blocking the treated blood vessel 15, and internal electrode 6 gradually becomes covered by thrombus material 19*d* removed from thrombus 19 due to the electrical field forces applied. As internal electrode 6 becomes covered by the thrombus material it may be needed to remove and clean, or replace it, for effectively dissolving further portions of the thrombus material 19 blocking blood vessel 15.

Catheter device 1 may be manufactured from any suitable type of biocompatible flexible and electrically isolating material, such as, but not limited to, plastic or silicone, by standard catheter manufacture processes as is well known in the catheter manufacture industry. The length of catheter device 1 may generally be in the range of 50 to 250 cm, preferably about 120-200 cm, and its outer diameter may generally be in the range of 1 mm to a few millimeters, preferably about 1.25 mm. The internal diameter of lumen 1*a* provided in catheter 1 may generally be in the range of 0.3 to 0.9 mm, preferably about 0.4 mm, and the internal diameter of lumen 1*b* may generally be in the range of 0.3 to 0.9 mm, preferably about 0.7 mm. The internal diameter of distal section 1*k* of lumen 1*b* may generally be in the range of 0.5 to 2.5 mm, and its length may generally be in the range of 7 to 25 mm, preferably about 15 mm. Electrodes 3 and 6 are placed inside their respective lumens 1*a* and 1*b* such that a gap 1*g* of about 2 to 30 mm is obtained between their distal tips.

It is noted that in certain preferred embodiments of the invention the electrode catheter may be configured without the enlarged distal section 1*k*, namely, such that the internal electrode is simply placed inside a the distal end section of lumen 1*b*.

Treatment electrode 3 is preferably made from a platinum wire having a diameter of about 0.01 to 4 mm, preferably about 0.3 mm, and a total length of about 5 to 50 mm, preferably about 20 mm. Treatment electrode 3 may be connected by soldering at connection point 4 to wire 5 and it preferably comprises an electrically isolating cover (not shown) having a thickness of about 0.1 mm, for isolating it from the blood in the treatment site. Wire 5 may be made of silver, copper, copper alloys, tin alloys, aluminum, titanium, electrically conducing material coated by copper or aluminum, or any other such electrically conductive wire material, having a diameter of about 0.2 to 1 mm, preferably about 0.5 mm, and comprising an electrically isolating cover (not shown) having a thickness of about 0.1 mm, for isolating it from the blood in the treatment site. The total diameter of wire 5 and its electrically isolating wire may generally be in the range of 0.5 to 1.5 mm.

The distance between the lumens of catheter 1 is preferably made as small as possible, as applicable depending on the materials from which it is made and the manufacture techniques used in manufacturing it.

Treatment electrode 3 is preferably configured such that its entire length is capable of being advanced out of catheter device 1 via the distal end opening of lumen 1a, into the blood vessel, in order to contact the thrombus material and in order for it to become attached to it during the treatment process, if so needed.

If thrombus-contacting electrode is made from platinum then internal electrode 6 may be made from a metallic material that does not include platinum, such as, but not limited to, silver, copper, copper alloys, tin alloys, aluminum, titanium, electrically conducing material coated by copper or aluminum, or any other such electrically conductive material. Internal electrode 6 is preferably formed as a plurality of spread-out multi-conductors having an opening angle of about 5 to 70 degrees e.g., comprising about 4 to 32 electrically conducting wires, in order to disperse electrical charges therefrom into the treatment site via the nearby blood. The diameter of internal electrode 6 may generally be in the range of 0.2 to 3.4 mm, preferably about 0.5 mm, (without the opening angle obtained by bristles 6b), and its length may be about 5 to 25 mm, preferably about 15 mm. Internal electrode 6 is electrically connected to a voltage source by means of an electrically isolated wire 7, and it is preferably placed about 10 mm behind the proximal end of treatment electrode 3. The two isolated wires, 5 and 7, may have similar properties (material, diameter, length, electrical isolation), and they preferably slidably pass along respective lumens, 1a and 1b, of catheter device 1 directed from the proximal end 1p to the distal end 1d.

According to one specific preferred embodiment of the invention one of the electrodes is made from titanium, copper alloy, or any other electrically conducting material coated by a silver or titanium layer, while the other electrode is made from platinum.

The surface area of the treatment and internal electrodes, 3 and 6, exposed to the blood in the treated site is preferably about 0.15 to 350 mm$^2$, and each of these electrodes should be made of a different conductive metal in order to provide ion migration there between.

Figure 1D:
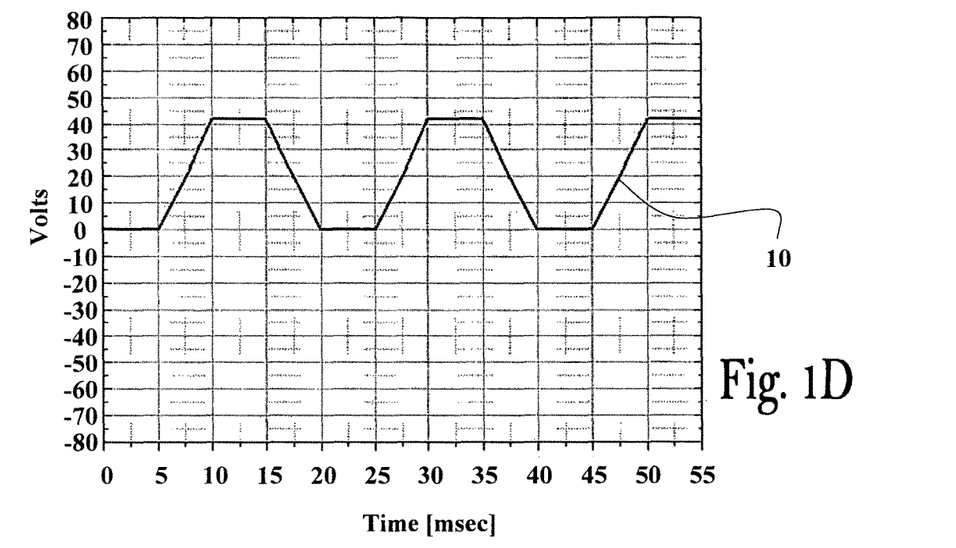

FIG. 1D shows an example of a preferred wave form that may be used with the electrodes of catheter device 1. As shown in FIG. 1D the electrical voltage signal 10 is a trapezoidal shaped signal which linearly ramps up from the ground level (0 volts) to a potential of about 40 volts over a time period of about 5 milliseconds, a more or less constant voltage level of about 40 volts is then maintained over a time period of about 5 milliseconds, it then linearly ramps down to ground level (0 volts) over a time period of about 5 milliseconds and remains in a constant ground level voltage over another time period of about 5 milliseconds, after which a new pulse is started as the signal ramps up again. Alternatively, the voltage signal may be comprised of the positive half waves of a sinus having biased about the ground level (0 volt), as obtained when passing a sinus signal through a diode anode. The frequency of signal 10 may generally be in the range of 0.1 Hz to 100 MHz, preferably about 50 Hz, and its pulse amplitude is preferably in the range of 1 volt to 100 volts, preferably about 42 volts, which ascertains minimal damage to the blood vessels or other compartments in the treated organ. Although other waveforms may be used with satisfactory results, the series of trapezoidal-shaped waves demonstrated in FIG. 1D was found to be advantageous in experiments carried out with the catheter device of the invention.

Figure 2:
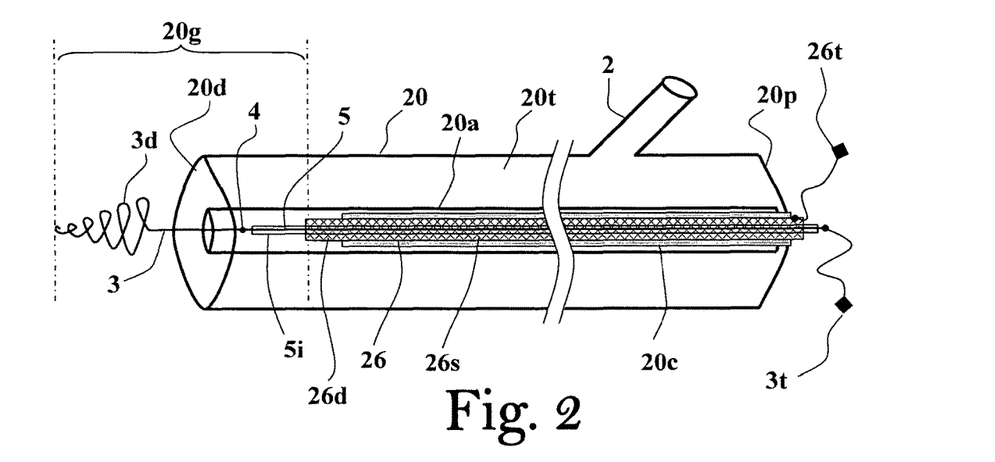
FIG. 2 schematically illustrates another preferred embodiment of the catheter apparatus of the invention comprising a pair of electrodes which are passed through a single lumen of the catheter apparatus.

FIG. 2 schematically illustrates another preferred embodiment of a catheter apparatus 20 of the invention comprising a pair of electrodes 3 and 26d which are passed through a single lumen 20a of catheter apparatus 20. In this preferred embodiment thrombus-contacting electrode 3 used is made more or less in the same structure and from similar materials as thrombus-contacting electrode 3 described hereinabove with reference to FIGS. 1A to 1C, and it therefore will not be discussed herein in details for the sake of brevity. As shown in FIG. 2, internal electrode 26d is passed together with the electrically conducting wire 5 of thrombus-contacting electrode 3 through the catheter lumen 20a. While internal electrode 26d may be passed inside lumen 20a adjacent to wire 5, in a preferred embodiment it is made in the form of a multistranded wire 26 in which electrically conducting strands 26s are braided over (or wrapped around) the electrically isolating layer 5i provided over wire 5. An electrically isolating cover 20c is preferably applied over a significant portion of conducting strands 26s such that its distal portion 26d remains exposed for serving as an internal electrode having length generally in the range of 7 to 25 mm, preferably about 15 mm.

Catheter apparatus 20 is made in a form of an elongate tube having a proximal end 20p and a distal end 20d, and it may be manufactured from similar materials as of catheter apparatus 1 discussed hereinabove utilizing standard catheter manufacture techniques as well known in the catheter manufacture industry. The inner diameter of lumen 20a may generally be in the range of 1 to 2.2 mm, preferably about 1.2 mm. Any suitable electrically isolating cover 5i may be used for electrically isolating between wire 5 and the braded strands 26s of internal electrode 26, preferably, a type of electrically isolating plastic material is used having thickness of about 0.1 to 0.5 mm. Internal electrode may be manufactured from similar materials as used in internal electrodes 6 discussed hereinabove with reference to FIGS. 1A to 1C, preferably, it is made from a multistranded wire made from platinum which strands are of about 0.01 to 0.5 mm in diameter. Terminals 3t and 26t may be respectively electrically coupled to the proximal ends of wire 5 and braided strands 26s of internal electrode 26, for applying electrical voltage signals as discussed herein above with reference to FIGS. 1B and 1C. Electrodes 3 and 26 are preferably arranged such that a gap 20g of about 2 to 30 mm is obtained between their distal tips.

Catheter apparatus 20 may be similarly used to carry out the dissolution or thrombectomy procedures as described hereinabove with reference to FIGS. 1B and 1C. However, whenever either electrode 3 or 26 of catheter apparatus 20 becomes covered with thrombus material, both electrodes 3 and are typically retracted proximally to be cleaned or replaced until the thrombus blockage is opened or removed.

In a preferred embodiment of the invention the entire catheter (including the electrode assembly), rather than just electrodes 3 and 26, may be withdrawn proximally.

According to one specific preferred embodiment of the invention both of the electrodes are placed outside of the catheter lumen(s). Accordingly, in such preferred embodiments carried out on the basis of the configurations shown in FIGS. 1 and 2, both of the electrodes will protrude distally out of their respective lumen(s) while maintaining a longitudinal distance of about 2 to 30 mm between their distal tips.

The longitudinal distance (e.g., 1g in FIG. 1A or 20g in FIG. 2) maintained between the tips of the electrodes should be configured in a way that will guarantee suitable electrical conductivity between the electrodes through the blood in the treatment site, while guaranteeing a sufficient distance of the internal electrode from the treated thrombus in order to prevent attachment thereof to the treated thrombus.

Typically, electrode catheters used in electro-surgery procedures are designed to produce heat by applying electrical charges to a relatively small area within a specific target zone. The electrical energy in these catheters is typically produced using electrical AC power sources, and their electrical properties are dictated by impedance matching considerations.

According to one preferred embodiment the catheter device of the invention is utilized for clot lysis by applying a tandem of voltage signals, preferably by applying monopolarized periodical alternating currents. The catheter device of the invention may be operated in two different modes:

i) Contacting the thrombus material with a positively charged electrode for attaching and retrieving it, or portions thereof, with the treatment electrode; or ii) Contacting the thrombus material with a negatively charged electrode for inducing electrical fields for a thrombus lyses process.

Catheterization Procedures

Figure 3:
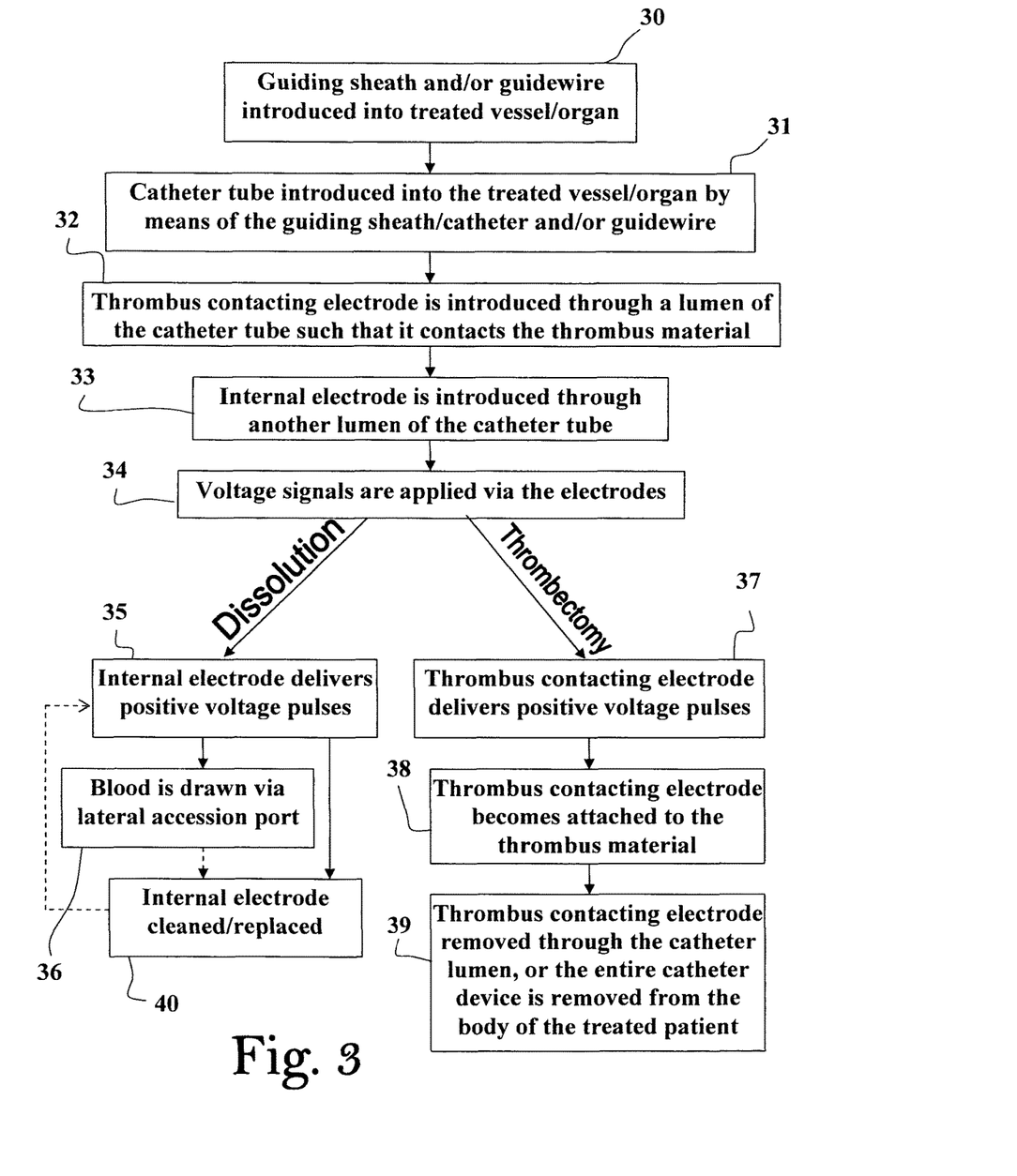
FIG. 3 is a flowchart illustrating exemplary dissolution/thrombectomy procedures carried out using the catheter apparatus shown in FIG. 1A.

With reference to FIG. 3, thrombus removal and/or dissolution may be carried out by means of catheter apparatus 1 (FIGS. 1A to 1C) according to the following steps:

1. The catheterization procedure may be based on the Seldinger method, gaining endovascular access by a peripheral vascular site (vein or artery) puncture and inserting a long or short sheath for further delivering guide-wire, the catheter device and the electrodes to the desired vascular treatment site (step 30). The peripheral access is typically a femoral or radial artery suitable for gaining access to the aorta and branches and to the brain and/or other body organs arteries.

2. The catheter device of the invention preferably has radio-opaque marks for visualization using x-ray imaging, and it is made from non-thrombogenic materials.

3. The procedure may generally require patient heparinization (e.g., 70 units Heparin per Kg)

4. After advancing a guiding sheath/catheter to the treatment site the catheter device of the invention is introduced into the guiding sheath. At the proximal end, the catheter (1) preferably has a lateral access port (2), or is connected to a "Y"-shaped connector, which can be used for connecting a syringe, or other such devices, suitable for drawing blood with debris and bubbles generated by the process. The blood drew back will also preserve the electrical circuit between the electrodes closed.

5. The lateral accession port 2, or "Y"-shaped connector can be also used for contrast injection for x-ray angiography.

6. The catheter is then navigated manually under angiographic fluroscopy to reach the nearest vessel to the thrombus to allow placement of the electrodes in the treatment site in proximal to the thrombus to be treated (step 31).

7. After positioning the catheter device, a first metal electrode-wire, also referred to herein as the treatment electrode or thrombus-contacting electrode, is inserted and advanced through a lumen of the catheter device (step 32). The electrode should have electrical isolation along its length such that the entire portion of its length between the distal end (1d) and the proximal end (1p) of catheter device (1) is electrically isolated, or alternatively, its electrical isolation may be implemented by a single wire directed through an additional lateral accession port which may be provided in the catheter (not shown), and which is designed to provide a lumen having electrical isolation properties. At the distal end (1d or 20d) of the catheter a portion of the electrode wire is exposed (3d) to be used as a thrombus-contacting electrode, said end section should protrude outwardly from the catheter and contact, preferably penetrate, the clot (after imaging its place by angiography).

8. The internal electrode-wire (can be a multi-conductor or a single wire) is preferably inserted through another lumen in the catheter (also with electrical isolation of the wire and/or lumen)(step 33). The end section of the internal electrode-wire, to be used as electrode, is exposed and embedded in blood drawn into the catheter through its distal opening. This electrode acts as an opposite charged electrode placed inside the catheter at a distance of few millimeters to centimeters from the tip of the treatment electrode. Alternatively, both of the electrodes are delivered with the catheter device as a single unit using the embodiments demonstrated in FIG. 1 or 2, such that the catheter device is advanced into the treatment site until the distal tip of the thrombus contacting electrode contacts the thrombus.

9. The electrodes are then connected to a voltage pulse generator that is able of producing unipolar pulses of about 1 to 100 V (or DC 1-100 V) (step 34). The treatment procedure may then proceed for carrying out Thrombectomy or Dissolution, as follows:

Thrombectomy: The treatment electrode should be positively charged (step 37) and embedded in the thrombus for allowing it to attach to the thrombus (step 38) and thereby assist in its removal/retrieval, by retracting the treatment electrode via its wire backwardly (proximally) into the catheter via its distal opening (step 39). The attached thrombus can also be retrieved together with the whole catheter device by retracting it proximally into the guiding catheter/sheath/shuttle which may be used in the treatment procedure. In general, this stage should take only a few minutes or less.

Dissolution: The pulse generator should be connected to the electrodes such that the treatment electrode contacting the clot is negatively charged (step 35), and thus facilitates its lyses by the negative charge. This stage should generally take a period of about 10 to 120 minute. In this configuration the internal electrode (placed inside the catheter) is positively charged, and therefore along the process the catheter might be occluded with thrombus generated in situ on the positive electrode. In this case, if drawing blood via the lateral accession port (step 36) will not remove the occlusion, the catheter should be taken out for cleaning, or be replaced (step 40) and returned to the treatment site for further operation, if so needed (indicated by broken lines).

Alternatively, the catheter apparatus of the invention may be pre-fitted with the thrombus-contacting electrode and the internal electrode, and their respective wires, already placed in their respective lumens, as described hereinabove. In this case steps 33 and 34 can be skipped since the catheter apparatus will be advanced with the electrodes placed in its lumens. In this mode the catheter device may be advanced with the thrombus-contacting electrode placed inside a distal section of its lumen such that it may be advanced distally to contact the thrombus material only after the catheter apparatus is placed in the treatment site.

It is to be noted that in one particularly preferred embodiment, the device of the present invention may be constructed such that the electrodes and their wires are freely slidable inside their lumen(s). However, in other preferred embodiments, the electrodes and their wires may be arranged such that they have no longitudinal movement, or limited longitudinal movement within their lumen(s).

EXAMPLE 1

Thrombus Preparation: The blood clot was prepared by incubating drained venous blood for 6 hours at room temperature, generating 2 cc whole blood red thrombus, in a 2 cm diameter plastic syringe.

Experiment: 10 cc heparinized blood, at a ratio of 1 unit Heparin per 1 cc blood ratio, was prepared in order to prevent spontaneous clotting of the blood added to the syringe. The catheter was placed in the syringe tube to allow the electrodes penetrate the thrombus, and heparinized blood was added to the tube for full covering of the thrombus with blood. Some blood was drawn back into the catheter.

The electrodes, one made of a platinum wire (0.6 mm diameter) and the other made of copper multi-conductor (1 mm diameter), were connected to an electrical voltage source generator. The electrical voltage source was activated to provide a 44 volts half-wave-pulse signal for a time-period of about 20 milliseconds, and the central (treatment) platinum electrode (embedded in the thrombus) was connected to the voltage source terminal of the negative polarity. Some blood was drawn back into the catheter in order to maintain completeness of the electrical circuit between the electrodes. After 30 minutes the voltage signal generator was turned off, and the copper (internal) electrode was pulled out for removing debris accumulated around the positive charged electrode. The electrode was then returned back into the tube, and the voltage signal generator was turned on in order to continue the process. The thrombus was dissolved after 50 minutes from the beginning of the experiment, and liquid blood started to flow through the syringe outlet. The thrombus size was reduced from 2 cc to less than 0.5 cc. Heating effects were not observed in the blood during the whole process.

The experiment included two syringes, one for carrying out the experiment and another one for control (the catheter was inserted but not connected to the generator). In the control syringe the clot remained at the size of 2 cc, unchanged.

The experiment was repeated five times, and the thrombus was significantly reduced in all said repetitions.

EXAMPLE 2

Thrombectomy

Background: The treatment electrode was positively charged and embedded in the thrombus for allowing it to attract the thrombus and thereby assist in its removal/retrieval, by retracting it backwardly (proximally) into the catheter via its distal opening. The animal model chosen is based on the publication: J. Gralla et al. "A Dedicated Animal Model for Mechanical Thrombectomy in Acute Stroke" *AJNR Am. J. Neuroradiol.* 27:1357-61 June-July 2006.

Positive periodic trapezoidal-shaped signal (as exemplified in FIG. 1D): provided via the thrombus contacting electrode (as exemplified in FIG. 1B).

Equipment & Materials

C-Arm angiography system (X-ray tube and imaging detector).
44 kg farm pig (female).
Pulsed power supply 42 V 50 Hz.
Digital oscilloscope.
Sheath F7.
Sheath F9.
Guiding wire F7.
Y connector.

Description

Animal Care: Sedation was induced by Ketmine 10 mg/kg and mg/kg midazolam, and endotracheal intubation was performed. The general anesthesia was maintained by 2% isoflurane inhalant. Vital parameters such as arterial blood pressure, heart rate, and expired oxygen and carbon dioxide levels were continuously recorded. The expired carbon dioxide levels were kept between 30 and 35 mm Hg. After the experiments the animal was euthanized with an intravenous injection of 20 m-mol potassium chloride.

The catheter was made of a pair of isolated wires: the internal electrode was made from a copper multi-conductor (0.5 mm diameter), and the treatment electrode was made from platinum single wire (0.3 mm diameter) wrapped around the central wire of the internal electrode. The electrical isolation was established by means of a plastic tube having a thickness of about 0.1 mm for each wire.

Failure Modes:
Animal distress—not observed.
Acute thrombosis complication—not observed.

Method:

Thrombus preparation: 4 mm diameter silicon pipes were filled with blood as the follows:
10 ml blood without contrast agent and without thrombin was incubated overnight before the experiment.
10 ml blood without contrast agent and with 0.01 ml thrombin was incubated for 60 minutes at room temperature.
10 ml blood with 1 cc Iodixanol (Visipaque 320) contrast agent with 0.01 ml thrombin was incubated for 60 minutes at room temperature.

Figure 4A:
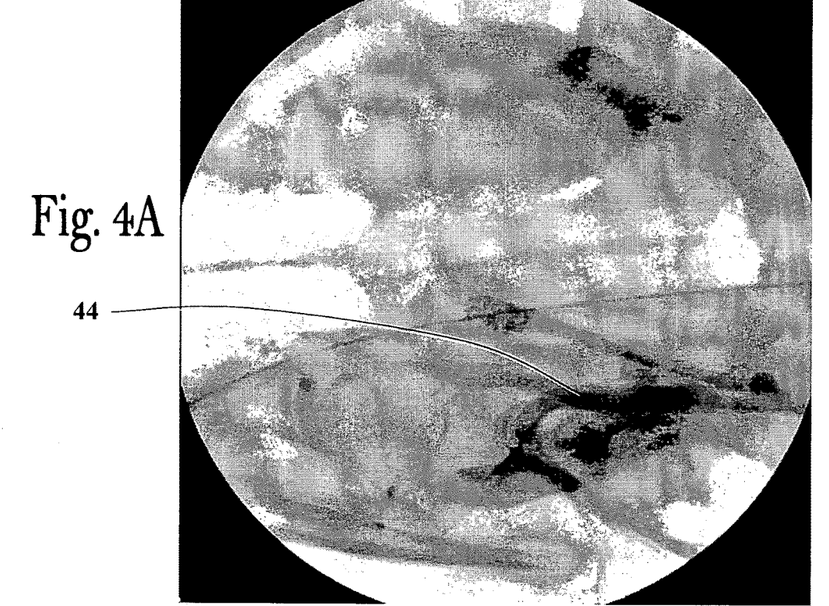
FIGS. 4A to 4E show images taken during the thrombectomy experiment described in example 2.
Figure 4B:
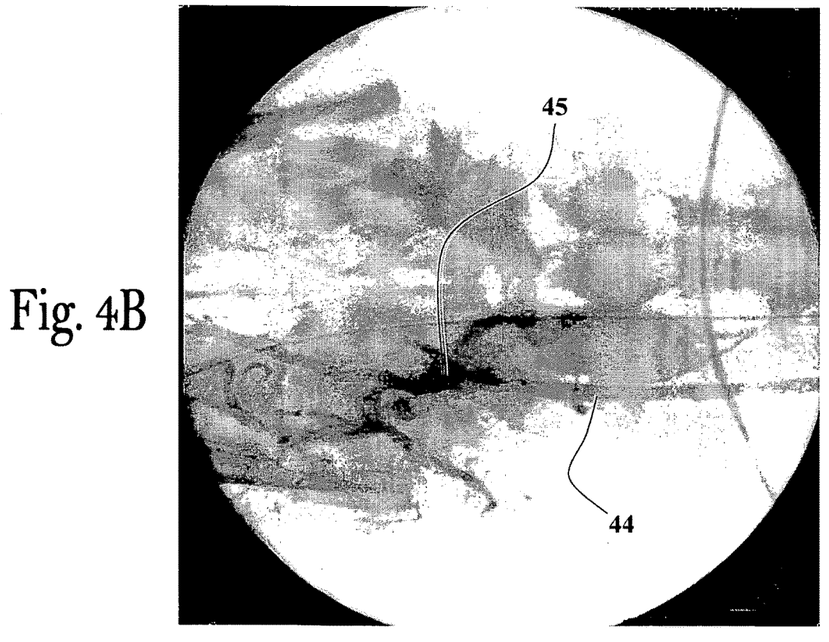
Figure 4C:
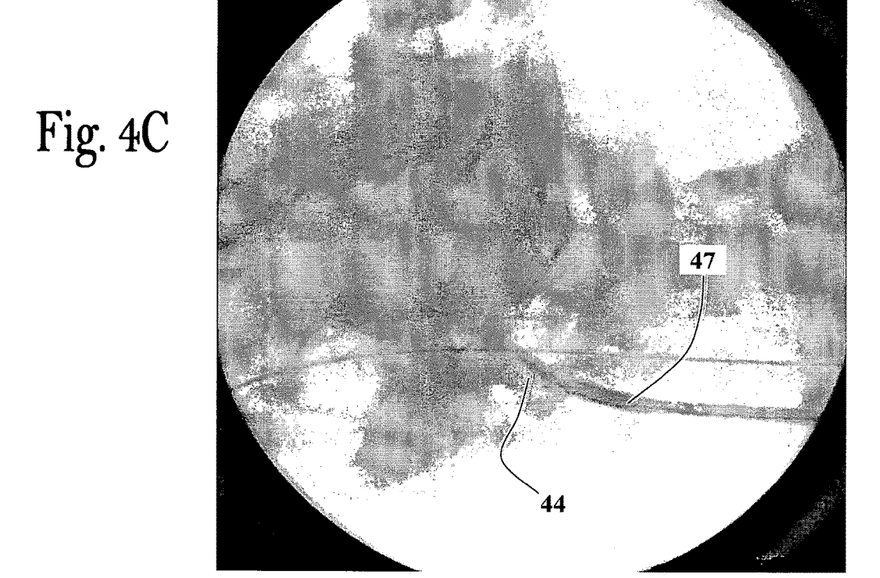

The catheter was led through a 1.7 mm sheath into the RT ICA:
Thrombus was generated by mixing 25 IU bovine thrombin and 10 mL autologous blood.
Locating the target artery for occlusion by injecting the thrombus through F9 catheter (FIG. 4A, treated artery designated by reference numeral 44).
The thrombus was placed inside the target artery.
Angiography demonstrated that the artery was occluded (FIG. 4B, thrombus designated by reference numeral 45).
The electrodes were delivered through the catheter to the target vessel until the central electrode was in contact with the thrombus. The electrodes were connected to a 42 Volt (50 Hz) pulsating power supply. The central (internal) electrode was connected to the positive (+) terminal of the power supply, and the internal electrode was connected to the negative terminal (FIG. 4C, catheter and electrodes designated by reference numeral 47).

After 5 minutes the electrode was attached to the thrombus and it was then detracted backward (proximally) into the catheter via its distal opening.

The thrombus was removed and found to be attached to the electrode that was pulled out (FIG. 5E showing thrombus material 49 attached to the electrodes of catheter 47).

Figure 4D:
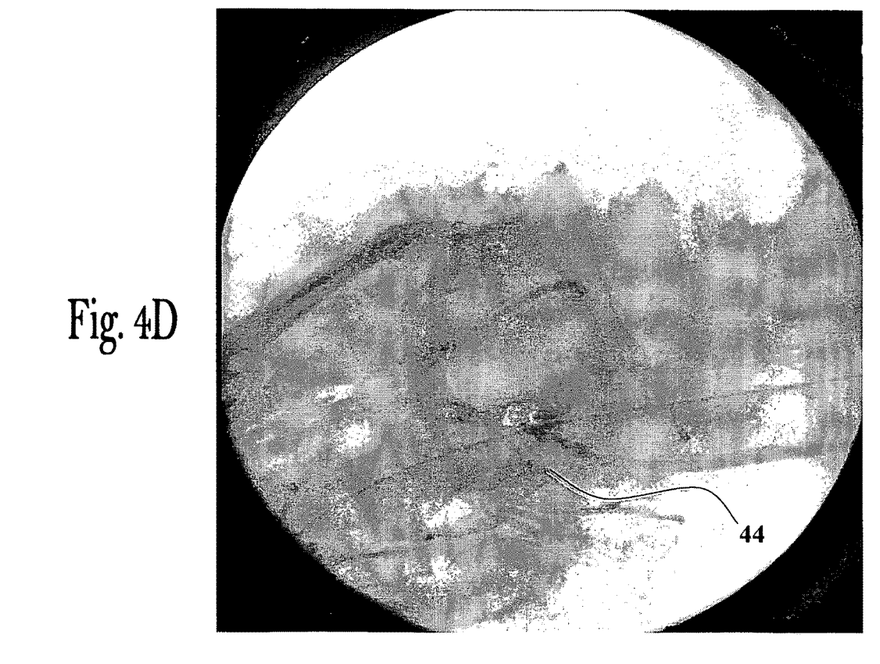
Figure 4E:
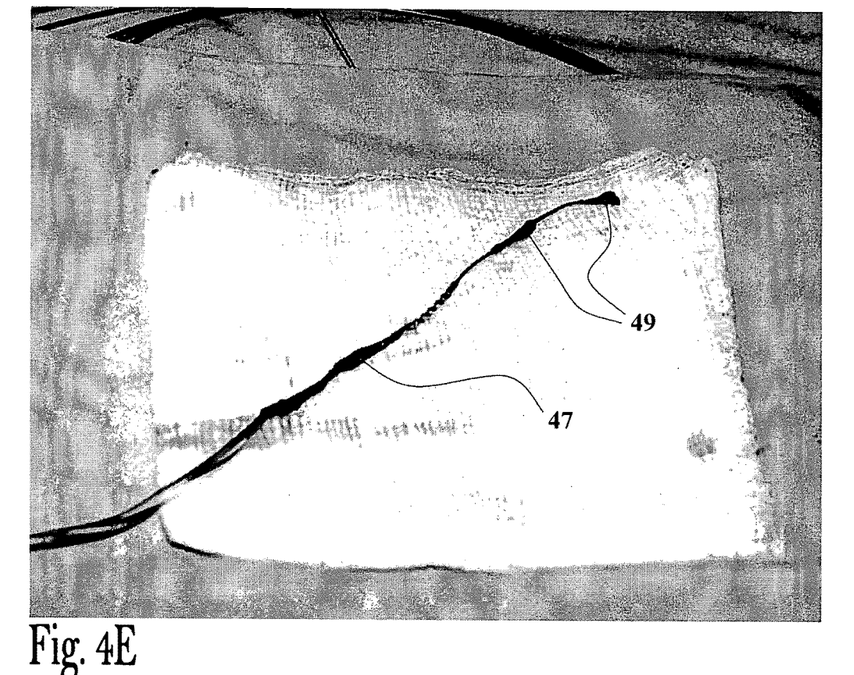

The imaging system showed reperfusion with good blood flow restoration in the previously occluded artery (FIG. 4D).

Recording of data:
Lab. Notebook.
Imaging CD-ROM.

EXAMPLE 3

Dissolution

The treatment electrode embedded in the thrombus is negatively charged, and thus will facilitate its lysis by the negative charge.

The animal model chosen is based on the publication: J. Gralla et al. "A Dedicated Animal Model for Mechanical Thrombectomy in Acute Stroke" AJNR Am. J. Neuroradiol. 27:1357-61 June-July 2006.

Equipment & Materials:
C-Arm angiography system (X-ray tube and imaging detector).
44 kg farm pig (female).
Pulsed power supply 42 V 50 Hz.
Digital oscilloscope.
Sheath F7.
Sheath F9.
Guiding wire F7.
Y connector.
Description/quantity to be tested:
Animal Care: Sedation was induced by Ketmine 10 mg/kg and 15 mg/kg midazolam, and endotracheal intubation was performed. The general anesthesia was maintained by 2% isoflurane inhalant. Vital parameters such as arterial blood pressure, heart rate, and expired oxygen and carbon dioxide levels were continuously recorded. The expired carbon dioxide levels were kept between 30 and 35 mm Hg. After the experiments the animal was euthanized with an intravenous injection of 20 m-mol potassium chloride.
The catheter was made of a pair of isolated wires: copper multi-conductor (0.5 mm diameter) and platinum single wire (0.3 mm diameter) wrapped around the central wire. The isolation was made of a 0.1 mm thickness plastic tube for each wire.
Failure Modes:
Animal distress—not observed.
Acute thrombosis complication—not observed.
Method:
Thrombus preparation: 4 mm diameter silicon pipes were filled with blood as follows:
10 ml blood without contrast agent and with 0.01 ml thrombin was incubated for 60 minutes at room temperature.
10 ml blood with 1 cc Iodixanol (Visipaque 320) contrast agent with 0.01 ml thrombin was incubated for 60 minutes at room temperature.
The catheter was lead through a 1.7 mm sheath into the ECA artery:

Thrombus was generated by mixing 25 IU bovine thrombin and 10 mL autologous blood one hour before the operation.

Figure 5A:
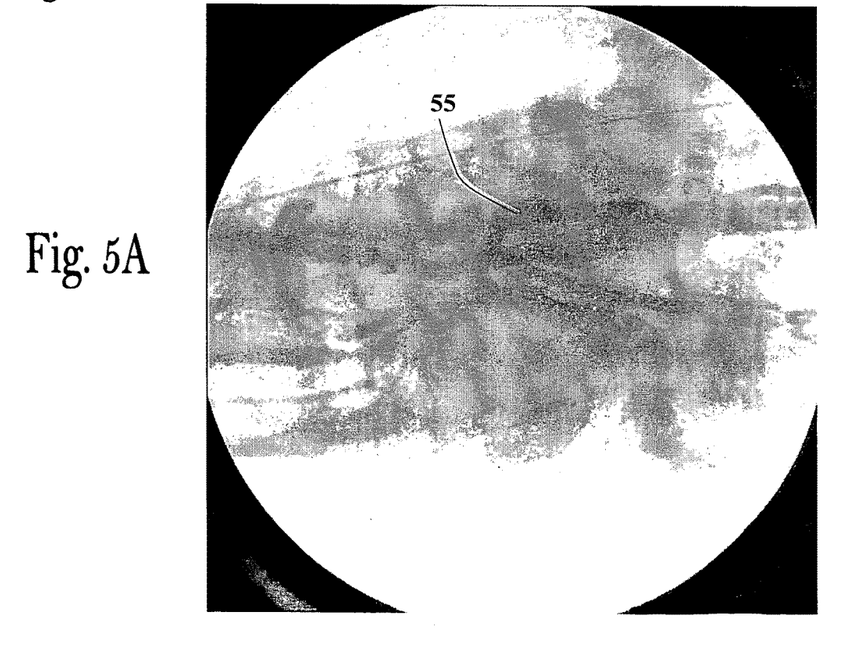
FIGS. 5A to 5D show images taken during the dissolution experiment described in example 3.

Locating the target artery for occlusion by injecting the thrombus through F9 catheter (FIG. 5A, treated artery is designated by reference numeral 55).

The thrombus was placed inside the target artery.

Figure 5B:
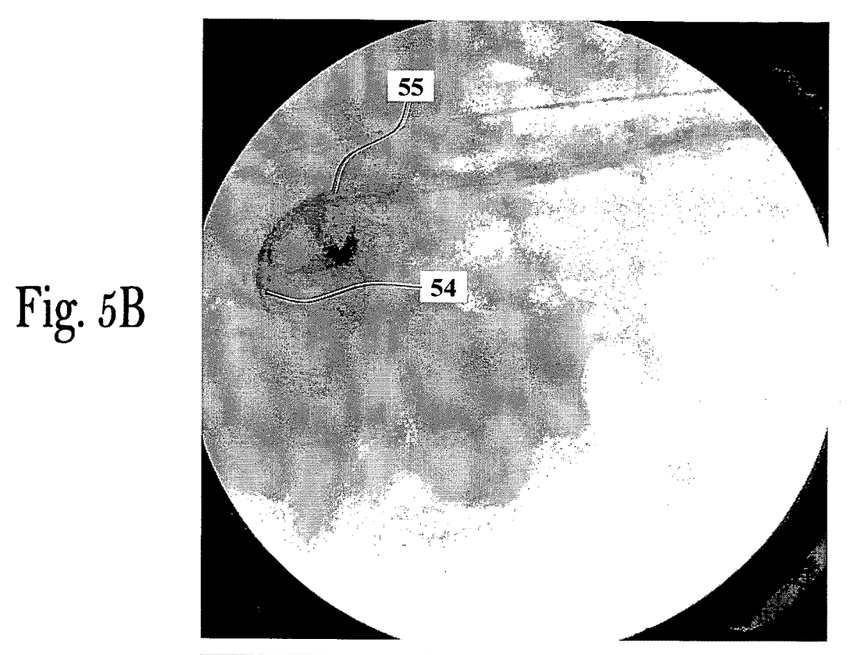

Angiography demonstrated that the artery was occluded (FIG. 5B, thrombus is designated by reference numeral 54).

Figure 5C:
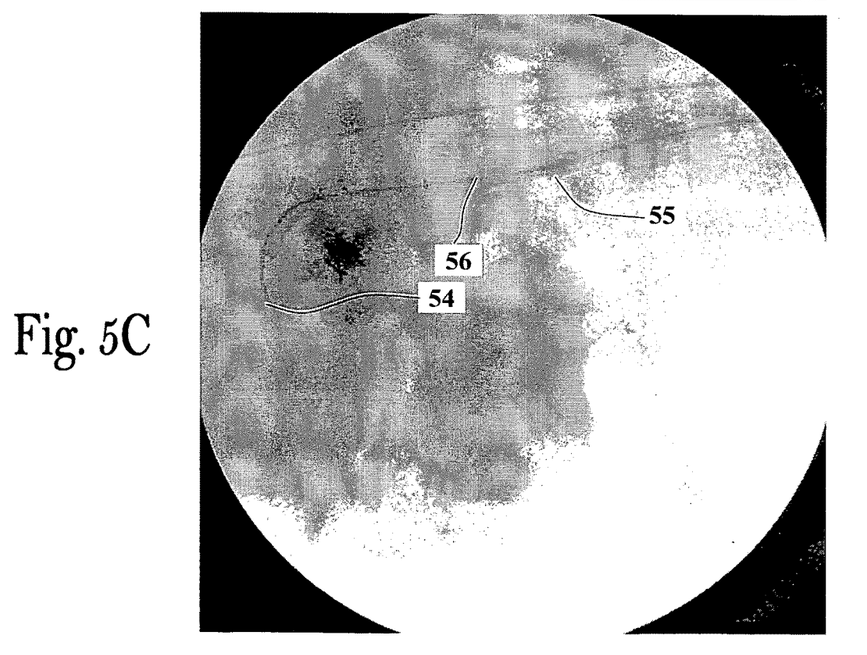

The electrodes were delivered through the catheter to the target vessel until the central electrode was in contact with the thrombus. The catheter was connected to the 42 Volt (50 Hz) pulsating power supply. The central electrode was connected to the negative (-) connector, and the wrapped around wire was connected to the positive connector (+) (FIG. 5C catheter and its electrodes are designated by reference numeral 56).

After 35 minute electrodes were pulled out.

Figure 5D:
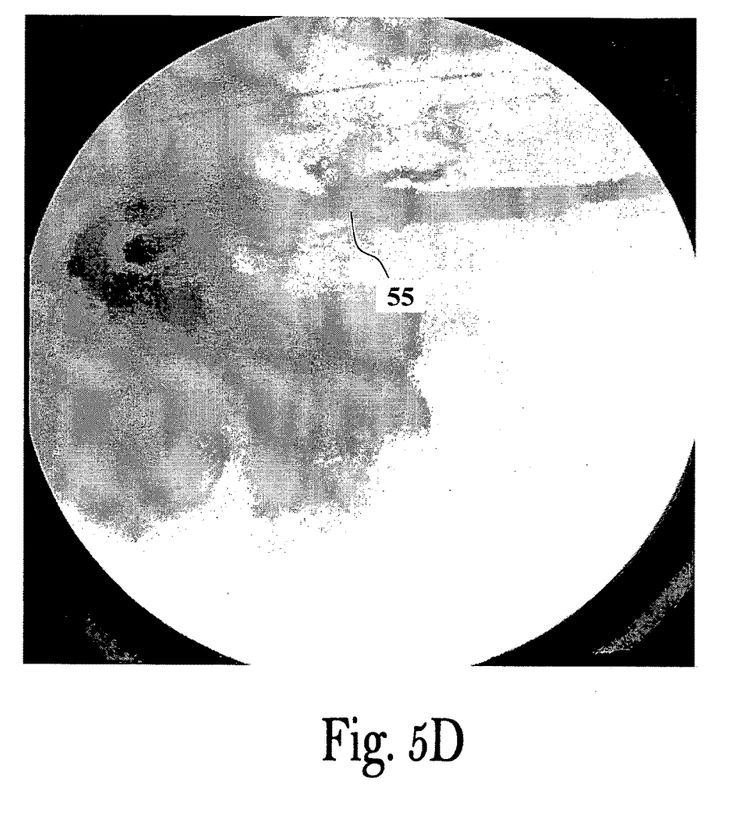

Angiography showed partially blood flow reperfusion in the previously occluded artery (FIG. 5D).

Recording of data:
Lab. Notebook.
Imaging CD-ROM

It is noted that the DC power time period needed in order to accomplish whole thrombus thrombolysis was found to be more than twice longer than the thrombosis producing time. Furthermore, by using low voltage and low frequency signals the risks of damaging blood vessels and/or other organs are substantially reduced or eliminated.

All of the abovementioned parameters are given by way of example only, and may be changed in accordance with the differing requirements of the various embodiments of the present invention. Thus, the abovementioned parameters should not be construed as limiting the scope of the present invention in any way. In addition, it is to be appreciated that the different lumens, tubes, wires, and other members, described hereinabove may be constructed in different shapes (e.g. having oval, square etc. form in plan view) and sizes differing from those exemplified in the preceding description.

The above examples and description have of course been provided only for the purpose of illustration, and are not intended to limit the invention in any way. As will be appreciated by the skilled person, the invention can be carried out in a great variety of ways, employing more than one technique from those described above, all without exceeding the scope of the invention.

The invention claimed is:

1. A method for removing a thrombus from a body of a subject, the method comprising:
   applying a unipolar voltage between a first wire and a second wire passing through at least one lumen of a tube,
   while a first electrode, which is connected distally to the first wire, is in contact with a thrombus in the body of the subject, and while a second electrode, which is connected distally to the second wire, is inside the at least one lumen of the tube; and
   subsequently to beginning application of the unipolar voltage, removing the thrombus from the body of the subject.

2. The method according to claim 1,
wherein applying the unipolar voltage comprises applying a positive voltage between the first wire and the second wire, such as to attach the first electrode to the thrombus, and
wherein removing the thrombus comprises removing the thrombus by retracting the first electrode.

3. The method according to claim 1,
wherein applying the unipolar voltage comprises applying the unipolar voltage by applying a negative voltage between the first wire and the second wire, such as to dissolve the thrombus into dissolved thrombus material, and
wherein removing the thrombus comprises removing the thrombus by removing the dissolved thrombus material.

4. The method according to claim 3, wherein the applying of the negative voltage causes the second electrode to become covered by the dissolved thrombus material, and wherein removing the dissolved thrombus material comprises removing the dissolved thrombus material by removing the second electrode from the body of the subject.

5. The method according to claim 1, wherein applying the unipolar voltage comprises applying the unipolar voltage while a distance between respective distal tips of the first electrode and the second electrode is between 2 and 30 mm.

6. The method according to claim 1, wherein applying the unipolar voltage comprises applying the unipolar voltage by applying a unipolar periodic pulse signal that includes a plurality of pulses.

7. The method according to claim 6, wherein one or more of the pulses are trapezoidal-shaped.

8. The method according to claim 6, wherein one or more of the pulses are half-waves of a sinusoidal signal.

9. The method according to claim 1, wherein applying the unipolar voltage comprises applying a direct current (DC) unipolar voltage.

10. The method according to claim 1, wherein applying the unipolar voltage comprises applying the unipolar voltage while one of the first electrode and second electrode is grounded.

11. A method for removing a thrombus from a body of a subject, the method comprising:
introducing a tube into the body of the subject;
passing a first wire, over which is an electrically isolating layer, through a lumen of the tube,
a first electrode being connected distally to the first wire,
a second electrode "being fixedly wrapped around the electrically isolating layer"is changed to being wrapped around and affixed to the electrically isolating layer, and
a second wire being connected to the second electrode;
subsequently to passing the first wire through the lumen, contacting the thrombus with the first electrode;
subsequently to contacting the thrombus with the first electrode, using a voltage source, applying a unipolar voltage between the first wire and the second wire while the first electrode is in contact with the thrombus; and
subsequently to beginning application of the unipolar voltage, removing the thrombus from the body of the subject.

12. The method according to claim 11, wherein applying the unipolar voltage comprises applying the unipolar voltage while the second electrode is inside the lumen of the tube.

13. The method according to claim 11, wherein applying the unipolar voltage comprises applying the unipolar voltage while a distance between respective distal tips of the first electrode and the second electrode is between 2 and 30 mm.

* * * * *